United States Patent [19]

Demain et al.

[11] 3,956,275

[45] May 11, 1976

[54] 2-DEOXYSTREPTOMYCIN

[75] Inventors: Arnold L. Demain, Wellesley, Mass.; Kozo Nagaoka, Yokohama, Japan

[73] Assignee: Massachusetts Institute of Technology, Cambridge, Mass.

[22] Filed: Jan. 20, 1975

[21] Appl. No.: 542,645

[52] U.S. Cl. ............................ 260/210 S; 195/80 R; 424/181
[51] Int. Cl.² ........................................ C07H 15/22
[58] Field of Search .................. 260/210 S, 210 AB

[56] References Cited
UNITED STATES PATENTS 2,837,510   6/1958   Yabuta et al. .................... 260/210 S
3,743,634   7/1973   Woo ................................ 260/210 S

OTHER PUBLICATIONS

Bock "The Jour. of Antibiotics," Vol. XXVII, No. 2, 1974, pp. 139–140.

*Primary Examiner*—Johnnie R. Brown
*Attorney, Agent, or Firm*—Arthur A. Smith, Jr.; Martin M. Santa; Anthony M. Lorusso

[57] ABSTRACT

A method of making new derivatives of streptomycin by mutational biosynthesis. A mutant of *Streptomyces griseus* makes streptomycin production dependent on streptidine addition.

A new antibiotic, deoxystreptomycin, is disclosed.

1 Claim, 2 Drawing Figures

2-DEOXYSTREPTOMYCIN

The invention herein described was made in the course of work performed with a grant from the Department of Health, Education and Welfare.

BACKGROUND OF THE INVENTION

The present invention is directed to the production of new derivatives of streptomycin by a technique called "mutational biosynthesis". This technique is disclosed in U.S. patent application Ser. No. 3,669,838 entitled Method of Making Antibiotics Containing the Aminocyclitol Subunit by Shier et al. A brief discussion of mutational biosynthesis appears below.

A culture ordinarily makes an antibiotic (ABC) composed of 3 moieties (A,B,C) from simple carbon and nitrogen sources:

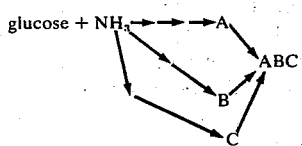

A mutant is obtained that cannot make A; thus, it cannot make the antibiotic ABC. If, however, A is fed in the medium, it can make the antibiotic.

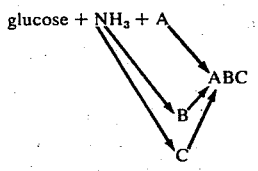

If instead of A, an analogue (A') is fed into the medium, the mutant can produce a new antibiotic (A'BC). Of course, the foregoing depends on the assumptions that:

A' will go into the cell; the incorporating enzyme is not too specific; and, A'BC has antibiotic activity.

At this point, it should be noted that the antibiotics disclosed in the Shier et al patent referred to above, contain 2-deoxystreptamine as its aminocyclitol.

Streptomycin is a different antibiotic in that it contains streptidine. It should also be noted that streptidine is most accurately characterized as a guanidinocyclitol rather than an aminocyclitol. The structural formulas for 2-deoxystreptamine and streptidine appear below.

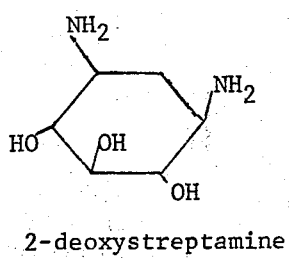

2-deoxystreptamine

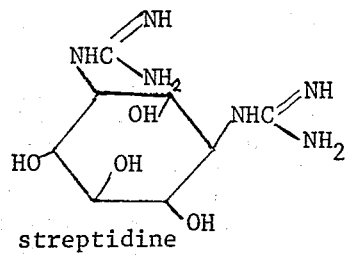

streptidine

The significance of the foregoing is that prior to the present invention, mutational biosynthesis had not been successful with antibiotics containing streptidine or analogues of streptidine. Indeed, in a doctorial thesis which can be obtained from the University of Illinois, Urbana, Illinois, entitled *The Hybrimycins* by W. T. Shier, the failure to produce the mutant required for streptomycin production by mutational biosynthesis is reported.

Mutational biosynthesis has been tried with *Bacillus circulans*, the producer of butirosins. This is another group of two antibiotics containing deoxystreptamine. Workers have also been successful in obtaining a deoxystreptamine mutant which could use streptamine and streptidine to form new antibiotics (DeFuria and Claridge, Abstr. Ann. Mtg. Amer. Soc. Microbiol., Miami Beach p. 13, 1973; Claridge et al., Devel. Industr. Microbiol. 15, 101, 1974)

There are similar studies on *Streptomyces kanamyceticus*, the producer of kanamycin, and on *Streptomyces ribosidificus*, the producer of ribostamycin. These are also deoxystreptamine-containing antibiotics. The deoxystreptamine mutant of *S. ribosidificus* could use 1-N-methyl-deoxystreptamine, streptamine, 2-epi-streptamine, and 3',4'-dideoxyneamine to make new active ribostamycin analogues containing these modified aminocyclitols. The *S. kanamyceticus* mutant could use 1-N-methyl-deoxystreptamine and epi-streptamine. These studies are described in Kojima and Satoh, J. Antibiotics 26, 784 (1973).

In Biochem. Biophys. Acta 148, 335 (1967) a study of the biosynthesis of streptomycin is disclosed and a cell-free enzymatic activity from *S. griseus* which phosphorylated streptidine in the presence of ATP is reported. The enzyme is also reported to be active on 2-deoxystreptidine, but, inactive on N-amidinostreptamine, N'-amidinostreptamine, N-amidinoinosamine and myoinositol. It was not known whether the enzyme had any role in streptomycin formation. It is also reported (Walker, Devl. Industr. Microbiol. 8, 109, 1967) that intact mycelia of all species of Streptomyces tested (except one) could phosphorylate streptidine even though many were not streptomycin producers. It has been suggested that such streptomycin non-producing species might possibly make streptomycin if fed streptidine or streptomycin analogues. It should be noted that the use of mutants of *S. griseus* in a mutational biosynthesis process has never been suggested. In J. Bacteriol. 99, 401 (1969) it was noted that the enzyme from *S. griseus* which phosphorylated streptidine and 2-deoxystreptidine also phosphorylated streptomycin at the same 6 position of streptidine and that the real function of the enzyme might be to inactivate streptomycin or to maintain it in an inactive form in the mycelium. The significance of the foregoing is that it has been known that deoxystreptidine acts as a substrate for an enzyme acting on streptidine.

SUMMARY OF THE INVENTION

In accordance with the present invention, it has been discovered that *Streptomyces griseus* can be mutated to a state of dependency on exogenous streptidine for the production of streptomycin and on streptidine analogues for the production of streptomycin derivatives by mutational biosynthesis.

Accordingly, an object of the present invention is to produce new derivatives of streptomycin by "mutational biosynthesis."

Another object of the invention is to produce the new compound "deoxystreptomycin."

Another object of the present invention is to produce a derivative of streptomycin in which 2-deoxystreptidine replaces streptidine.

A further object of the invention is to mutate *Streptomyces griseus* to a state of dependency on exogeneous streptidine for the production of streptomycin.

DESCRIPTION OF THE PREFERRED EMBODIMENTS

Figure 1:
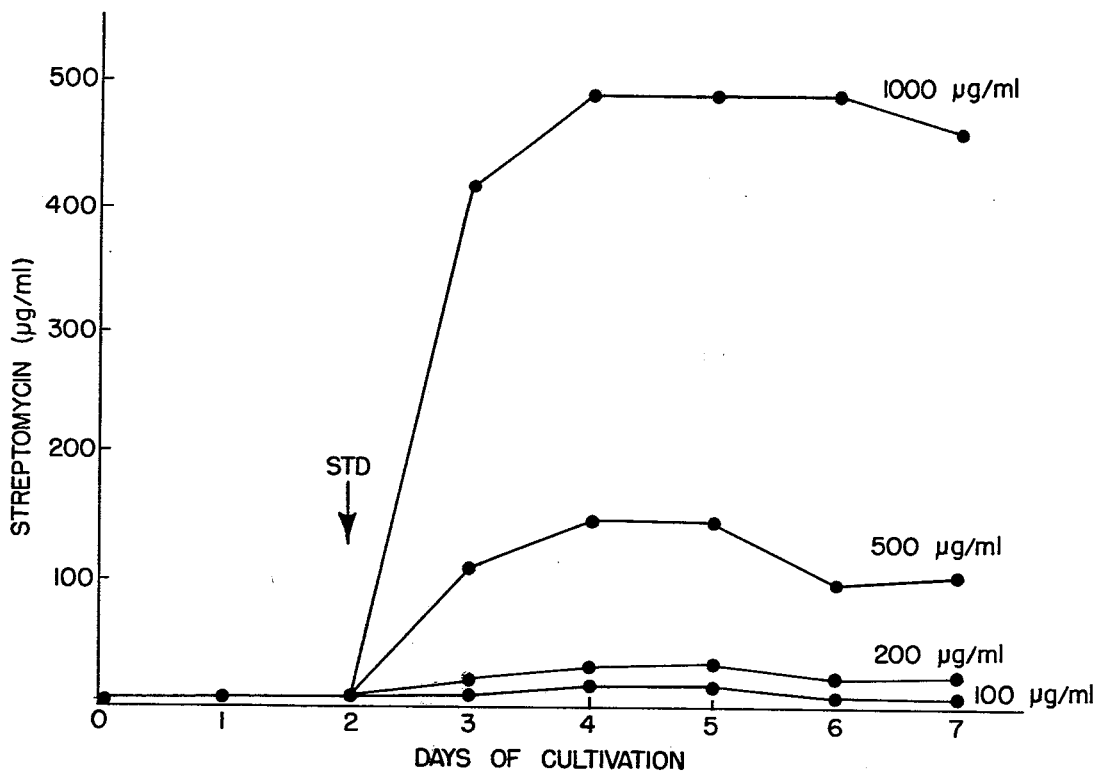
FIG. 1 is a graph showing the results of streptidine dependent productions of streptomycin by the mutant of the present invention.

At the outset, the present invention is described in its broadest overall aspects with a more detailed description following. In accordance with the present invention, micro-organisms producing streptidine containing antibiotics are genetically converted to mutants which cannot produce the antibiotic without streptidine supplementation. For example, a mutant of *Streptomyces griseus* has been isolated which produces no antibiotic unless streptidine is added to the medium. This mutant has enabled a group of antibiotics to be obtained which contain a guanidinocyclitol group or subunit as part of the molecular structure. Among the guanidinocyclitol antibiotics which can be produced by this mutant are streptomycin A, streptomycin B and their derivatives.

In the normal production of an antibiotic, the microorganism is grown in an aqueous medium containing a soluble carbohydrate, a source of assimilable nitrogen and essential mineral salts. During growth, the microorganism biosynthesizes the guanidinocyclitol subunit and incorporates it into the antibiotic formed as a metabolic product. If a guanidinocyclitol other than the one normally formed by the microorganism is microbiologically incorporated into the metabolic products, new products having antibiotic activity are produced.

It has been found according to the present invention that mutants of microorganisms known to produce antibiotics containing guanidinocyclitols can be formed which lack the capacity to biosynthesize the guanidinocyclitol subunit but have the capacity to utilize an added guanidinocyclitol molecule to form an antibiotic. When the added guanidinocyclitol molecule is different than the guanidinocyclitol subunit present in the antibiotic produced by the unmutated microorganism, a new antibiotic is produced. However, when the added guanidinocyclitol molecule is the same as the guanidinocyclitol subunit present in the old antibiotic produced by the unmutated microorganism, the mutated microorganism will produce the old antibiotic. The invention thus provides the method of making an antibiotic containing a guanidinocyclitol subunit, comprising cultivating or growing a mircroorganism mutant in an aqueous medium containing a soluble carbohydrate, a source of assimilable nitrogen, essential mineral salts and an added guanidinocyclitol, said mutant being incapable of biosynthesizing the guanidinocyclitol molecule but which molecule the unmutated microorganism biosynthesizes in the formation of an antibiotic when cultivated in a nutrient medium having no added guanidinocyclitol, continuing growing the mutant until substantial antibiotic activity is imparted to the culture medium and separating the antibiotic from the medium. Details for the preparation of the mutant appear below.

PREPARATION OF THE MUTANT

Mutants of antibiotic-producing microorganisms blocked in biosynthetic pathways so as to be incapable of forming the guanidinocyclitol subunit can be formed by treating conidia with N-methyl-N'-nitro nitrosoguanidine. For example, a representative method of obtaining a desired mutant is to treat a monoconidial suspension of microorganism spores grown on a vegetable juice agar medium with N-methyl-N'-nitro nitrosoguanidine (0.5 mg/ml) in a 0.05M phosphate buffer (pH 7.0) to kill nearly all the microorganisms, inoculate Petri plates containing vegetable juice agar with the survivors, incubate until sporulation occurs and replica plate to Petri plates containing nutrient agar with and without an added guanidinocyclitol normally biosynthesized by the unmutated microorganism. Following incubation, the plates are overlaid with agar seeded with *Bacillus subtilis* or some other test organism, and then incubated. The plates are then screened for a colony showing a zone of inhibition on nutrient agar containing the added guanidinocyclitol but no zone of inhibition on nutrient agar containing no added guanidinocyclitol. In this way, a suitable mutant is located, after which a stock culture of that organism is isolated from the master plate. The mutant so isolated will grow on a defined medium at approximately the same rate as the unmutated microorganism.

In accordance with the foregoing procedure, a monoconidial suspension of *S. griseus* was mutagenized with nitrosoguanidine in phosphate buffer at pH 7.0 for 5 hours.

Percent kill was 99.5%

Streptomycin non-producing mutants and streptidine-dependent mutants were selected by overlaying colonies with agar seeded with *B. subtilis*.

Non-production was checked by the agar plug method.

Among 834 colonies tested, 8 non- or low-producing mutants and 1 streptidine-dependent mutant were obtained. Thus, one streptidine-dependent mutant was obtained out of 834 colonies of *S. griseus* derived from conidia which survived mutagenesis. This mutant has been deposited in the American Type Culture Collection, 12301 Parklawn Drive, Rockville, Maryland, 20852, on an unrestricted basis and has been given number ATCC 31087. This mutant has also been designated as MIT-A5 and is available to the public on an unrestricted basis by writing to the Massachusetts Institute of Technology. This mutant (MIT-A5) can be obtained from the Department of Nutrition and Food Science, Massachusetts Institute of Technology, Cambridge, Massachusetts 02139.

ANTIBIOTIC PRODUCTION

The invention also provides a process of growing the mutants so produced and isolated, in a nutrient medium containing an added guanidinocyclitol to produce one or more novel antibiotics. Processing for the isolation and recovery of the antibiotics are also provided. The medium used can be the same as is normally used to grow the unmutated microorganism, in the absence of an added guanidinocyclitol, and will contain at least water, a soluble carbohydrate, a source of assimilable nitrogen and essential mineral salts. Since the guanidincyclitols are bases, they are readily added as the free base or in the form of an acid addition salt such as the hydrochloride or sulfate salt. Submerged fermentation on shakers for 96 hours at 28°C, is usually employed for maximum growth and antibiotic production. However, variations in growth conditions may be desirable from one mutant to another so the person skilled in the art should make adjustments to achieve the best results.

After growth is terminated, the broth is filtered and is treated with a suitable anion exchange resin, advisably on the ammonium cycle, to absorb the antibiotic. The resin is then washed with ammonium hydroxide or dilute hydrochloric acid to elute the antibiotic. The eluates are concentrated under reduced pressure and then subjected to paper chromatography to separate and purify the antibiotic.

By growing the *S. griseus* mutant (MIT-A5) in this way and in the presence of added 2-deoxystreptidine, a new antibiotic, deoxystreptomycin, is obtained.

The structure of streptomycin A appears below:

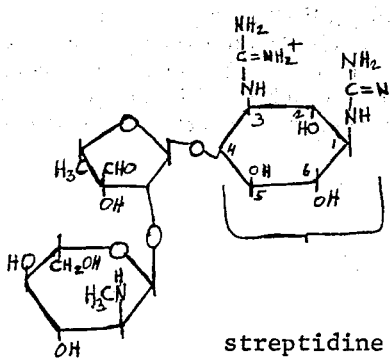

streptidine

Streptidine is a guanidino-cyclitol and is a component of the streptomycin molecule. Streptomycin producing *S. griseus* can synthesize streptidine from glucose via myo-inositol. However, with the mutant of the present invention, the biosynthetic pathway of streptidine is blocked; but, this mutant can utilize exogenous streptidine for streptomycin biosynthesis.

To produce new derivatives of streptomycin in accordance with the present invention analogues of streptidine may be substituted for the exogenous streptidine. For example, 2-deoxystreptidine may be substituted for streptidine. The structure of 2-deoxystreptidine appears below; and, as can be seen from the structural formula, when the oxygen in the number 2 position of the streptidine molecule is removed, 2-deoxystreptidine results.

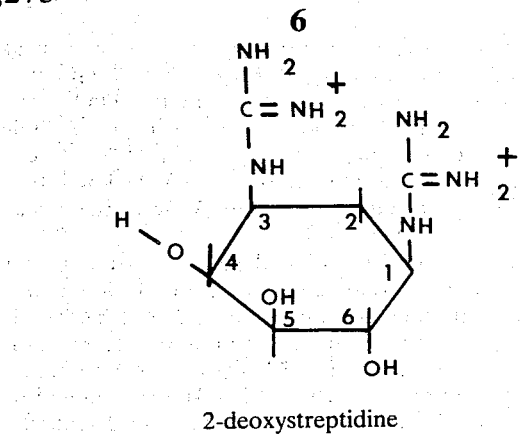

2-deoxystreptidine

2-Deoxystreptidine may be prepared from deoxystreptamine in accordance with the procedure set forth in an article entitled Streptomycin Biosynthesis.Enzymatic Synthesis of O-Phosphorylstreptidine from Streptidine and Adenosinetriphosphate by J. B. Walker and M. S. Walker, Biochem. Biophys. Acta 148. pp. 335 (1967), the teachings of which are incorporated herein by reference. It should be noted that the method of preparing 2-deoxystreptidine appearing in the foregoing article is a method for preparing radioactive 2-deoxystreptidine. Of course, for purposes of the present invention, the 2-deoxystreptidine should be prepared in a non-radioactive manner. The resulting streptomycin derivative, i.e. 2-deoxystreptomycin, which can be prepared by utilizing exongenous 2-deoxystreptidine has the following formula:

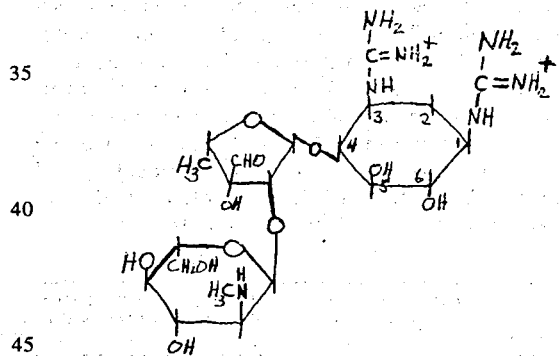

FIG. 1 shows the result of streptidine-dependent production of streptomycin by the mutant MIT-A5. After 48 hours, streptidine hydrosulfate in the range of 0 to 1,000 ug/ml was added to the culture as is shown by the four curves in FIG. 1. No detectable amount of antibiotic was produced without streptidine supplementation. The amount of streptomycin produced increased in accordance with the amount of streptidine added. By the addition of 1,000 ug/ml streptidine about 500 ug/ml of streptomycin was accumulated in the culture. Production reached its peak 2 days after the addition of streptidine.

Figure 2:
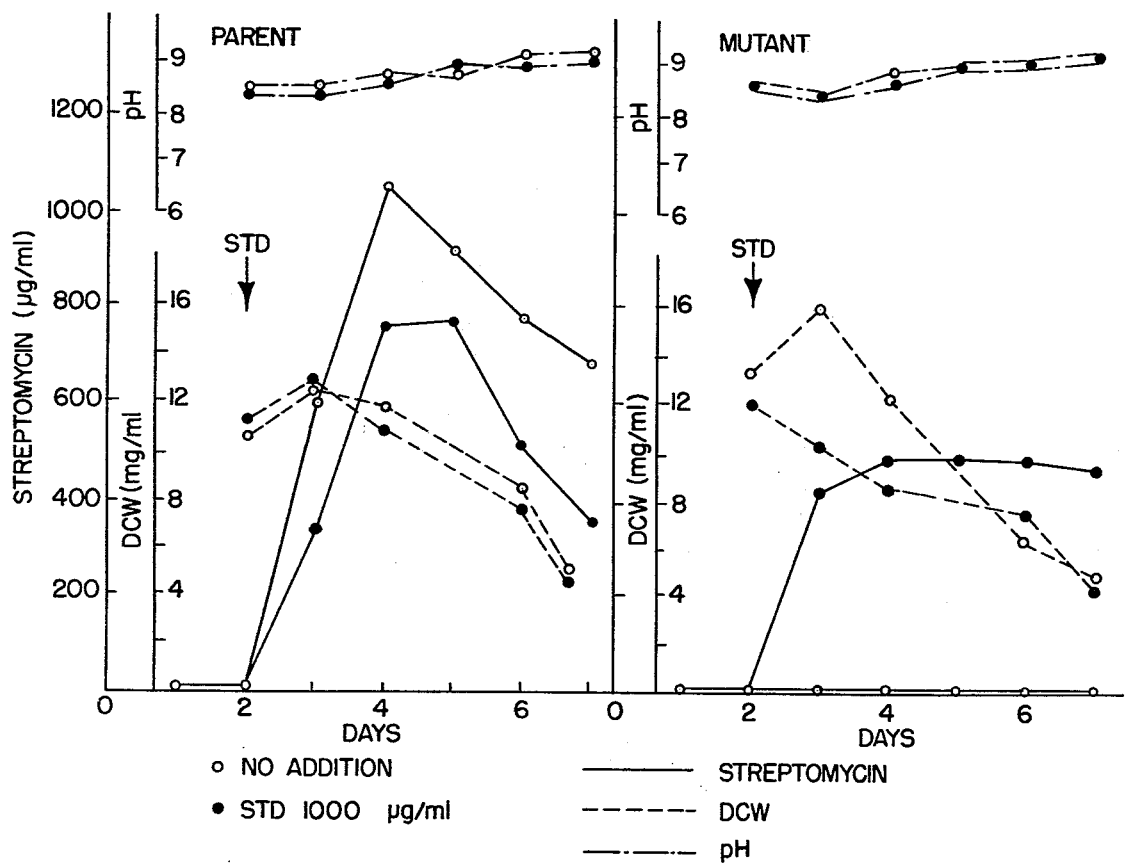
FIG. 2 is a graph which illustrates the effect of streptidine addition to parent and mutant cultures.

The effect of streptidine addition on the production of streptomycin, growth and pH change by the parent and mutant strain are shown in FIG. 2. Open circles indicate the control values and solid circles indicate the values of the streptidine supplemental culture. Although streptomycin production by the mutant was completely dependent upon the addition of streptidine, production by the parent strain was inhibited somewhat by streptidine addition. No difference in pH pattern was observed. Parental growth was not affected by streptidine; but, growth of the mutant was somewhat inhibited by the addition of 1,000 ug/ml streptidine. The antibiotic substance produced by the mutant was analyzed by paper chromatography. The product migrated at the same rate as streptomycin in three solvent systems. Another fermentation experiment showed that no antibiotic substance was produced by supplementation of myo-inositol to the mutant.

Table I shows streptidine-dependent streptomycin production by a resting cell suspension of the mutant. After growth, the cells were washed and suspended in Tris buffer with or without streptidine. The reaction mixtures were shaken at 28°C for 48 hours. Streptomycin was synthesized in accordance with the amount of streptidine added and the relative cell concentration.

| Mixed vegetable juice (V-8 juice) | 20 ml |
| Calcium carbonate | 0.3 g. |
| Agar | 2.0 g. |
| Distilled water to 100 ml. | pH 7.0 (NaOH) | was inoculated from stock culture of *S. griseus* 7-455F3. After incubation for 6 days at 28°C., spores from a slant were suspended in 5 ml of the following spore suspension medium:

| Aerosol O. T. (Diactyl Sodium Sulfosuccinate) | 0.005% |
| NaCl | 0.5 |
| $MgSO_4$ | 0.05 |

TABLE I

PRODUCTION OF STREPTOMYCIN BY CELL SUSPENSIONS OF THE MUTANT

| ADDITION ($\mu$G/ML) | RELATIVE CELL CONCENTRATION | INCUBATION TIME | | | | | |
|---|---|---|---|---|---|---|---|
| | | 0 HR | | | 48 HRS | | |
| | | pH | DCW$^a$ (MG/ML) | SM$^b$ ($\mu$G/ML) | pH | DCW (MG/ML) | SM ($\mu$G/ML) |
| NONE | 1 X | 7.2 | 5.2 | <10 | 8.2 | 2.5 | <10 |
| STREPTIDINE 250 | 1 X | 7.2 | 5.2 | <10 | 8.0 | 2.1 | 48 |
| STREPTIDINE 500 | 1 X | 7.2 | 5.4 | <10 | 8.2 | 2.5 | 150 |
| STREPTIDINE 1000 | 1 X | 7.1 | 5.4 | <10 | 8.2 | 2.7 | 200 |
| NONE | 2 X | 7.2 | 10.2 | <10 | 8.3 | 4.6 | 12 |
| STREPTIDINE 1000 | 2 X | 7.2 | 11.0 | <10 | 8.9 | 5.4 | 400 |

$^a$Dry Cell Weight
$^b$Streptomycin

Several aminocyclitols have been tested preliminarily by the agar-plug method for their ability to support production of new antibiotics with the mutant. All deoxystreptamine analogues have failed to elicit antibiotic activity. Only streptidine and 2-deoxystreptidine gave antibiotic activity. It is not known, however, whether the inactivity with deoxystreptamine analogues is due to impermeability, to the specificity of the incorporation enzyme, or the lack of bioactivity of streptomycins containing deoxystreptamine derivatives. The results are set forth in Table II.

TABLE II

PRODUCTION OF ANTIBIOTICS BY SUPPLEMENTATION WITH AMINO - OR GUANIDINO - CYCLITOL DERIVATIVES

| ADDITIONS | CONC. ($\mu$G/ML) | ANTIBIOTIC PRODUCTION |
|---|---|---|
| NONE | — | NEGATIVE |
| DEOXYSTREPTAMINE | 200 | NEGATIVE |
| 1-N-METHYLDEOXYSTREPTAMINE | 200 | NEGATIVE |
| STREPTAMINE | 200 | NEGATIVE |
| N-MONOACETYLSTREPTAMINE | 200 | NEGATIVE |
| N,N'-DIACETYLSTREPTAMINE | 200 | NEGATIVE |
| 2-EPI-STREPTAMINE | 200 | NEGATIVE |
| STREPTIDINE | 200 | POSITIVE |
| DEOXYSTREPTIDINE | 200 | POSITIVE |

At this point, it should be noted that the invention is not intended to be limited to the procedures set forth in the examples which follow, but rather these examples are provided in order to teach one skilled in the art how to practice the invention and thus are not intended to limit the invention in any way.

EXAMPLE I

Preparation of *S. griseus* mutant MIT-A5 (ATCC 31087)

A mutant of *S. griseus* was prepared by treatment of *S. griseus* 7-455F3 with N-methyl-N'-nitro-nitrosoguanidine. A slant containing 5 ml of the following medium (V-8 agar medium) in distilled water. The spore suspension thus obtained was passed through a sterilized Nucleopore filter (25 mm. in diameter and pore size 8$\mu$). This procedure was necessary to obtain a monoconidial suspension.

To a flask containing 20 ml of sterilized 0.05M phosphate buffer (pH7.0), 2.5 ml of 5 mg/ml solution of N-methyl-N'-nitro-N-nitrosoguanidine in the same buffer and 2.5 ml of the above-mentioned monoconidial suspension were added. This flask was incubated 5 hours with rotary shaking. Petri plates containing 20 ml of the V-8 agar were inoculated with a diluted suspension of the organism in the flask and incubated at 28°C. until sporulation of the resulting colonies occurred. Spores were transferred by the replica plating technique to Petri plates containing 20 ml of Nutrient agar (Difco) which had been autoclaved for 20 minutes at 20°C. Spores from the same V-8 agar plate were also transferred by the same technique to Petri plates containing the same medium plus 200 $\mu$g/ml of streptidine hydrosulfate. The Petri plates were incubated 44 hours at 28°C. at which time 8 ml of another medium was added to the plates. This medium was Bacto Streptomycin assay agar sterilized at 120°C. for 15 minutes, cooled to 46°C. and seeded with 0.1 ml spore suspension of *Bacillus subtilis* per 250 ml of the assay agar.

The plates were stored at 5°C for 1 hour and incubated at 28°C for 14 hours. The plates were examined for a colony that showed a zone of inhibition on the medium containing streptidine hydrosulfate but no zone of inhibition on the medium lacking streptidine hydrosulfate. The mutant MIT-A5 was isolated from the V-8 agar plate.

The isolated streptidine-negative mutant grows in a streptomycin production medium at approximately the same rate as the unmutated *S. griseus*. Antibiotic production showed a linear dependence on added streptidine in the range of 50 μg/ml and 1 mg/ml by assay against *B. subtilus*.

By growing the mutant MIT-A5 on a nutrient agar medium containing the guanidinocylitol 2-deoxystreptidine, a new antibiotic, deoxystreptomycin, is obtained. Examples follow to illustrate the production, recovery, concentration and purification of the new antibiotic.

EXAMPLE 2

Fermentation of *S. griseus* Mutant MIT-A5 on Agar

The mutant, *Streptomyces griseus* MIT-A5, was grown in streak cultures in 20 Petri dishes containing 20 ml of Nutrient agar supplemented with 20 mg. of deoxystreptidine hydrosulfate per 100 ml of Nutrient agar for 48 hours at 28°C. The contents of the Petri plates were pooled, frozen, thawed, filtered, and the filtrate passed down a column of 25 ml. of a cation exchange resin, Amberlite IRC-50, in the sodium form. The column was washed with 1 liter of deionized water, and eluted with 100 ml of 1N hydrochloric acid. The eluate was evaporated under reduced pressure (0.2 mm), the residue extracted with 3.0 ml of methanol followed by concentration to 1 ml and 20 μl applied to chromatographic paper (Whatman No. 20). The materials were chromatographed with water-saturated n-butanol containing 2% p-toluene sulfonic acid monhydrate. The location of the antibiotic was visualized by placing the chromatogram on the surface of 500 ml of medium (Bacto Antibiotic Medium 5) that had been autoclaved for 15 min., cooled to 48°C. and mixed with 0.2 ml of a suspension of spores of *Bacillus subtilis*, then allowed to set in a 9 by 16 inch dish. After 15 min. the paper was removed, and the medium incubated at 28°C. for 20 hr. Zones of inhibition of growth of *B. subtilis* indicate the location of antibiotic on the original chromatogram. The antibiotic from the mutant of *S. griseus* MIT-A5 had two antibacterial spots corresponding to the Rf values of 0.35 and 0.08.

EXAMPLE 3

Production of Deoxystreptomycin A and Deoxystreptomycin B

To produce deoxystreptomycin A and deoxystreptomycin B, test tube slants containing 5 ml of V-8 agar medium were prepared.

After sterilization, spores of *S. griseus* mutant MIT-A5 were inoculated, incubated 6 days at 28°C. and good spore formation was obtained.

To the slant, 5 ml of distilled water was added to prepare a spore suspension. Flasks, containing 36 ml of production medium - glucose 2%; Bacto-soytone 2%; corn steep liquor 2%; yeast extract (Difco) 0.2%, pH 7.3 (before sterilization) — were sterilized at 120°C. for 15 minutes. After cooling, 0.1 ml of spore suspension was inoculated into each flask. Flasks were shaken for 24 hours at 28°C.; then, 4 ml of sterilized 2-deoxystreptidine solution (10 mg/ml) were added. After 48 hours, the culture broth was centrifuged and the antibiotic activity of the supernatant was assayed using *B. subtilis* ATCC 6633.

The antibiotic activity of the supernatant was 21 μg/ml when it was calculated as streptomycin A.

Ten ml of this filtrate was concentrated in vacuo to one-tenth of the original volume.

Five hundred μl of this sample were applied to Whatman No. 1 filter paper and the chromatogram was developed for 24 hours at room temperature using water saturated n-butyl alcohol containing 2% p-toluene-sulfonic acid monohydrate.

Bioactive spots were detected at Rf 0.35 and 0.08.

Antibiotic which was detected at Rf 0.35 will be called deoxystreptomycin A and that detected at 0.08 will be called deoxystreptomycin B.

Bioactive zones of the paper chromatogram corresponding to the spots of Rf 0.35 and 0.08 were cut out. After drying they were soaked in ethyl ether to remove P-toluene sulfonic acid and were eluted with distilled water separately.

In this method two antibiotics were efficiently separated (13 μg of deoxystreptomycin A and 5 μg of deoxystreptomycin B were obtained from 500 μl of concentrated culture filtrate.)

Deoxystreptomycin is a broad-spectrum bactericidal antibiotic of use in fighting infectious disease of humans, animals and plants caused by Gram-positive and Gram-negative bacteria. It is especially useful against tuberculosis.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. 2-Deoxystreptomycin.

* * * * *